United States Patent [19]

Genese et al.

[11] 4,316,460
[45] Feb. 23, 1982

[54] GRAVITATIONAL FLOW SYSTEM FOR THE SEQUENTIAL ADMINISTRATION OF MEDICAL LIQUIDS

[75] Inventors: Joseph N. Genese, Waukegan; Andrew J. Muetterties, Gages Lake, both of Ill.

[73] Assignee: Abbott Laboratories, North Chicago, Ill.

[21] Appl. No.: 167,948

[22] Filed: Jul. 14, 1980

Related U.S. Application Data

[63] Continuation-in-part of Ser. No. 16,227, Feb. 28, 1979, abandoned, and Ser. No. 16,228, Feb. 28, 1979, Pat. No. 4,223,695, and Ser. No. 16,230, Feb. 28, 1979, Pat. No. 4,250,879, and Ser. No. 16,232, Feb. 28, 1979, Pat. No. 4,219,022, and Ser. No. 16,461, Feb. 28, 1979, Pat. No. 4,256,104.

[51] Int. Cl.³ .............................................. A61M 5/00
[52] U.S. Cl. .............................................. 128/214 R
[58] Field of Search ........... 128/214 R, 214 C, 214 G, 128/227

[56] References Cited

U.S. PATENT DOCUMENTS 3,886,937  6/1975  Bobo et al. ..................... 128/214 G
3,993,066  11/1976 Virag .............................. 128/214 C
4,223,695  9/1980  Muetterties ..................... 128/214 R Primary Examiner—John D. Yasko
Attorney, Agent, or Firm—Robert S. Beiser; Robert L. Niblack

[57] ABSTRACT

A gravitational flow system for the sequential administration of medical liquids to a patient comprises a primary container connected to a primary tube, a secondary container connected to a secondary tube, and a combined air barrier and liquid sequencing valve which connects them and is in fluid communication with a common tube extending to the patient. A primary flow control device is positioned in the primary flow path and a secondary flow control device is positioned in the secondary flow path. In operation the system dispenses primary liquid unless interrupted by a flow of secondary liquid. In that instance, primary liquid flow is cut off by an air capturing pocket. At the same time, a plurality of air barriers prevent infusion of air into the patient.

22 Claims, 5 Drawing Figures

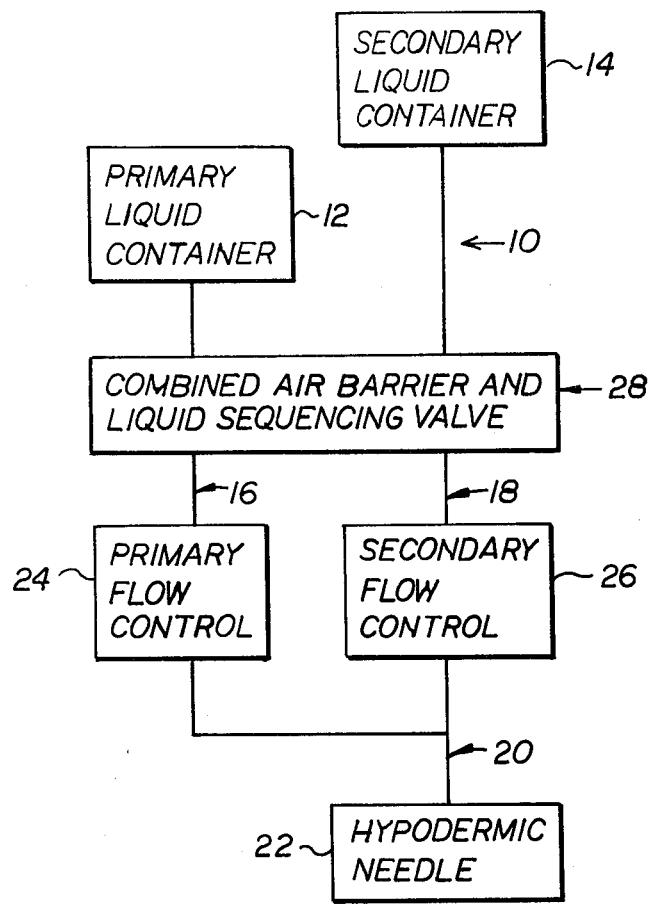
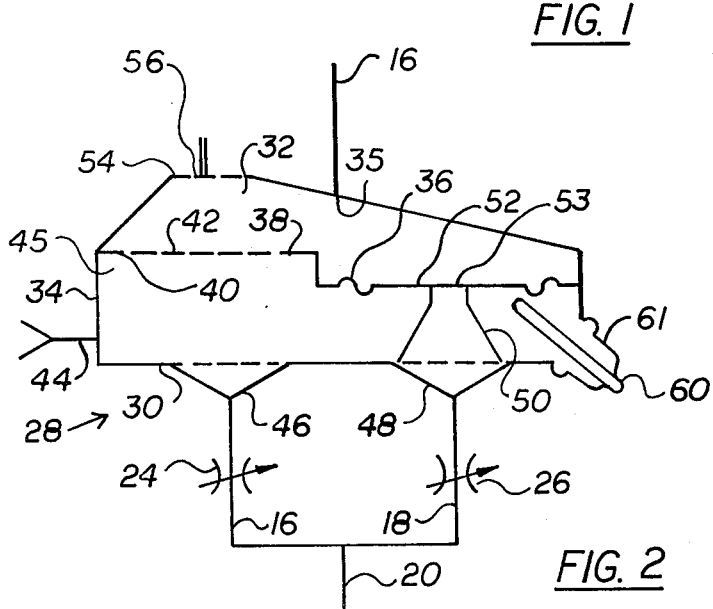

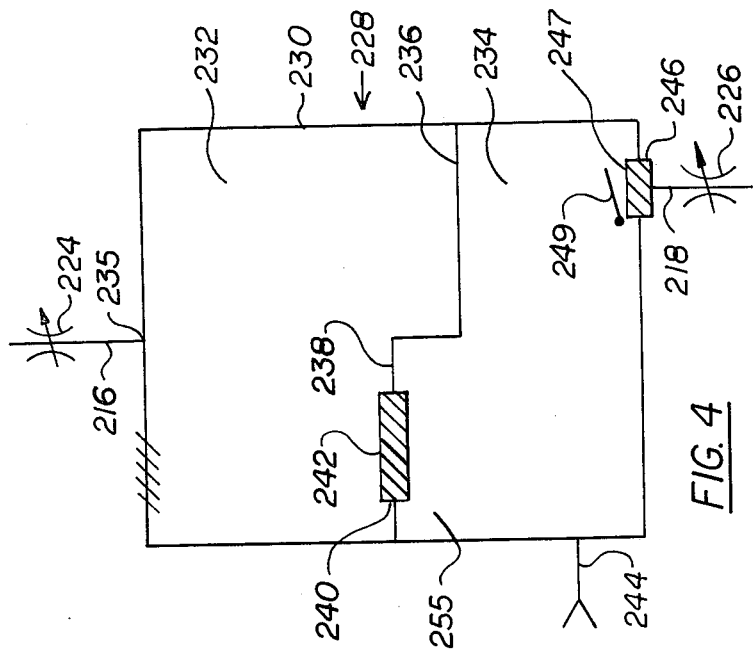
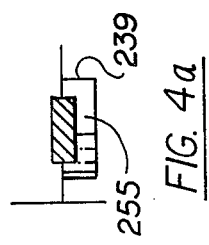
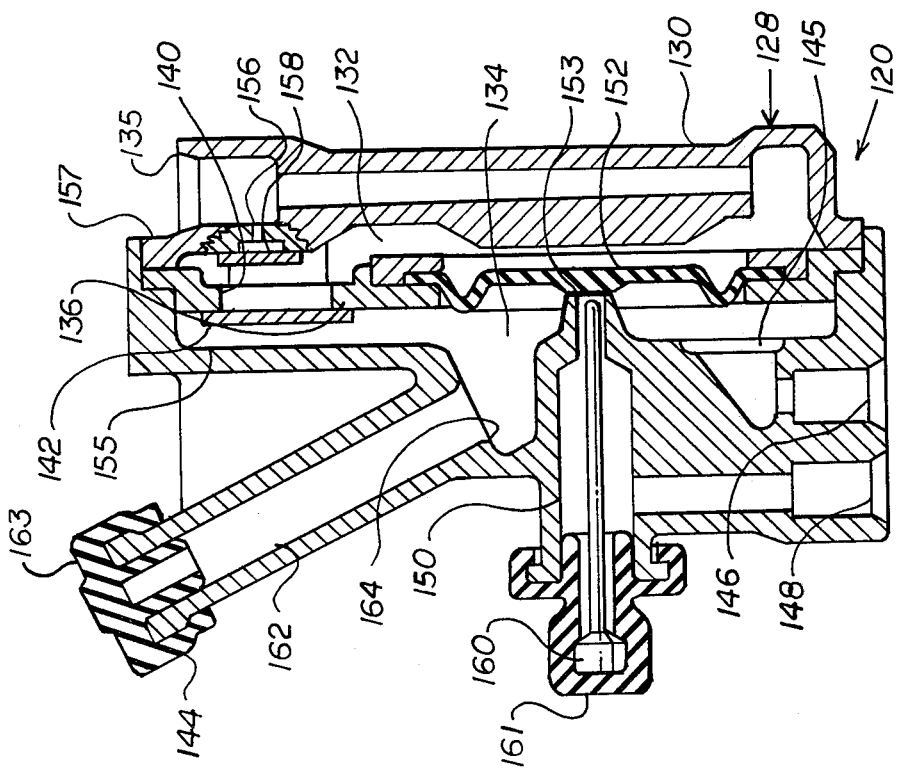

GRAVITATIONAL FLOW SYSTEM FOR THE SEQUENTIAL ADMINISTRATION OF MEDICAL LIQUIDS

BACKGROUND OF THE INVENTION

This application is a continuation-in-part of U.S. Ser. Nos. 16,277 abandoned; 16,228 now U.S. Pat. No. 4,223,695; 16,230 now U.S. Pat. No. 4,250,879; 16,232 now U.S. Pat. No. 4,219,022; and 16,461 now U.S. Pat. No. 4,256,104, all filed Feb. 28, 1979.

The present invention relates to systems and equipment sets for the administration of medical liquids to a patient, and more particularly, to systems and equipment sets for the sequential administration of a plurality of medical liquids employing a novel air capturing pocket in the flow path of one liquid to prevent the passage of liquid through that path when a second liquid is being dispensed.

The parenteral administration of medical liquids to patients is a long established practice. Liquids including amino acids, dextrose, electrolytes, and saline are commonly administered to patients over prolonged periods of time. Generally, these liquids are administered from a glass bottle or plastic bag suspended above the patient and containing 250–1,000 ml. of the liquid. Such prolonged infusions commonly are administered at a flow rate of 10–150 ml./hr.

Frequently, the patient must receive an additive or secondary liquid while the prolonged infusion is being administered. Preferably, this secondary liquid should be administered through the same hypodermic needle to avoid unnecessary pain and trauma to the patient of additional venipunctures. To avoid dilution and incompatability problems, it is also preferable that the flow of the primary liquid employed in the prolonged infusion be temporarily interrupted, the secondary liquid administered and the flow of the primary liquid resumed. Generally, the secondary liquid will be administered at a flow rate of 50–250 ml./hr.

Abbott Laboratories, North Chicago, Ill. manufactures a y-type set for the sequential administration of primary and secondary liquids. These VENOSET® piggyback sets allow the prolonged infusion of a primary liquid to be temporarily halted by means of a backcheck valve in the primary flow path to administer a secondary liquid without the need for a new venipuncture. Then, when the secondary liquid has been depleted, the backcheck valve automatically opens to resume flow of the primary liquid. An important characteristic of this system is that the secondary liquid container must be suspended at a higher height than the primary liquid container to establish the liquid pressure differential that closes the backcheck valve in the primary liquid flow path.

A similar system is disclosed in U.S. Pat. No. 3,886,937 granted June 3, 1975 to D. Bobo, et al, assigned to American Hospital Supply Corporation, and entitled "Medical Administration Set for Dispensing Plural Medical Liquids." Another similar system is disclosed in U.S. Pat. No. 4,105,029 granted Aug. 8, 1978 to R. Virag, assigend to Baxter Travenol and entitled "Intraveous Solution Set Having An Air Access Site and Constricted Inner Diameter Portion."

An inherent disadvantage of the above-mentioned prior art medical liquid administration systems is that they each resume the flow of primary liquid at the rate the secondary liquid had been flowing. Because the preferred rate of the secondary liquid is generally greater than the preferred flow rate of the primary liquid, when the primary liquid resumes flow at that rate, the patient can be administered an excessive amount of primary liquid, unless the flow rate of the primary liquid is adjusted to the preferred primary liquid flow rate soon after the flow of primary liquid resumes.

A remedy to the above-described disadvantage would appear to be provided by simply incorporating flow control devices into both the primary and secondary liquid flow paths. However, while this remedy does provide dual flow rates for the primary and secondary liquids, it is unacceptable. That is, because the common tube of the y-set must be able to accommodate both flow rates, when the primary liquid is flowing at a slower rate than the secondary liquid was, there will be an unfilled volume or void in the common tube. To fill that void, air will be drawn into the common tube from the depleted secondary container. That air will then be driven into the patient by the weight of the primary liquid, thereby causing a serious embolism and perhaps, the patient's death.

Various filter systems for the prevention of air passing into the common tube of a medical liquid administration set are exemplified by U.S. Pat. Nos. 3,854,907 (Rising), 3,149,758 (Bush), and 4,116,646 (Edwards), all assigned to Millipore Corporation. All of these devices utilize a hydrophilic membrane filter. However, the combining of an air barrier sequencing valve with a primary and secondary liquid sequencing function and the further use of preset primary and secondary flow controls was first disclosed in U.S. Ser. No. 16,228 filed Feb. 28, 1979, of which this application is a continuation-in-part.

From the foregoing, it will be apparent that an efficacious system for the sequential administration of medical liquids at dual flow rates would be advantageous to the medical profession.

SUMMARY OF THE INVENTION

The primary object of the present invention, therefore, is to provide an equipment set for the sequential administration of medical liquids at preset dual flow rates that will not draw air from the secondary container when the secondary liquid has been depleted.

In accordance with this and other objects, there is provided by the present invention a gravitational flow system comprising a primary container in fluid communication with a primary tube, a secondary container at a height greater than that of the primary container, in fluid communication with a secondary tube, and an air barrier and liquid sequencing valve connected to the primary and secondary tubes with a common tube extending to the patient. A primary flow control is positioned in the primary flow path for adjusting the rate of flow of primary liquid through the primary liquid flow path at a rate independent of the secondary liquid. Similarly, a secondary flow control is positioned on the secondary liquid flow path for adjusting the flow rate of the secondary liquid therethrough. The combined air barrier and liquid sequencing valve allows primary liquid to flow whenever the height of the primary liquid is greater to or equal than the height of the secondary liquid, but prevents primary liquid from flowing when the primary container is at a height less than the height of the secondary container in the system.

In a preferred embodiment the previously mentioned air barrier and liquid sequencing valve comprises a housing divided into first and second chambers by a substantially horizontal partition. The partition includes a raised platform portion having an outlet port incorporated therein for the passage of primary liquid from the first chamber to the second chamber. The outlet port includes a hydrophilic membrane incorporated therein which covers the port and prevents air from moving between the two chambers when it is moistened by liquid. The second chamber includes an inlet port for secondary liquid and an outlet port at the bottom thereof for the passage of primary or secondary liquid. As a result, when secondary liquid passes into the second chamber, residual air is trapped below the platform and hydrophilic membrane, so as to create an air trap, thereby preventing the flow of primary liquid.

In another embodiment of the invention, the second chamber also includes a reservoir incorporated therein having a flexible diaphragm member disposed across and selectively sealing its upper portion and an outlet port at the bottom thereof for the passage of secondary liquid from the second chamber. When secondary liquid passes into the second chamber the diaphragm is displaced upwardly from the top of the reservoir due to the greater pressure of the secondary liquid. Secondary liquid enters the reservoir and passes out the outlet port at the bottom.

The primary flow control is positioned on the portion of the primary tube connected to the outlet port at the bottom of the second chamber. The inlet port to the first chamber for the primary liquid is preferably at the top. The inlet port to the second chamber for secondary liquid is preferably at the side. The secondary flow control is positioned on the secondary tube leading from the outlet port of the reservoir.

In a preferred embodiment, the combined air barrier and liquid sequencing valve may include a closable air vent. The air vent is preferably covered by a hydrophobic membrane which prevents the passage of liquid from the chamber but allows air to be displaced during priming of the system.

BRIEF DESCRIPTION OF THE DRAWINGS

FIG. 1 of the drawings is a block diagram of an improved gravitational flow system for the sequential administration of medical liquids to a patient.

FIG. 2 of the drawings is a schematic diagram of one embodiment of the combined air barrier and liquid sequencing valve of FIG. 1.

FIG. 3 of the drawings is a side cutaway view of an alternate embodiment of the combined air barrier and liquid sequencing valve of FIG. 1.

FIG. 4 of the drawings is a schematic diagram of an alternative embodiment of an improved air barrier and liquid sequencing valve.

FIG. 4A of the drawings is a partial cutaway view of an alternative embodiment of the air capturing pocket employed in the combined air barrier and liquid sequencing valve of FIG. 4.

DETAILED DESCRIPTION OF THE PREFERRED EMBODIMENT

While this invention is susceptible to embodiment in many different forms, there is shown in the drawings, and will herein be described in detail, several specific embodiments with the understanding that the present disclosure is to be considered as an exemplification of the principles of the invention and is not intended to limit the invention to the embodiments illustrated.

As seen in FIG. 1 of the drawings, improved gravitational flow system 10 comprises a primary liquid container 12, a secondary liquid container 14, a primary tube 16, in fluid communication with primary liquid container 12 a secondary tube 18 in fluid communication with secondary liquid container 14, a common liquid tube 20 in fluid communication with both primary liquid tube 16 and secondary liquid tube 18 and a hypodermic needle 22 at the proximal end of common tube 20. Interposed on primary tube 16 is primary flow control 24 which regulates the rate of flow of the primary liquid. Similarly interposed on secondary tube 18 is secondary flow control 26 which controls the flow of secondary liquid. Interposed in both primary tube 16 and secondary tube 18 are a combined air barrier and liquid sequencing valve 28 which permits the flow of primary liquid when the primary liquid container 12 is at a height equal to or greater than the secondary liquid container 14. However, when secondary liquid container 14 is at a height greater than primary liquid container 12 combined air barrier and liquid sequencing valve 28 prevents the flow of primary liquid and allows the flow of secondary liquid.

Combined air barrier and liquid sequencing valve 28 as seen in FIG. 2 comprises a housing 30 divided into first chamber 32 and second chamber 34 by a substantially horizontal partition 36. Primary liquid from primary tube 16 enters first chamber 32 through port 35. Incorporated into partition 36 is a raised platform portion 38 having an outlet port 40 incorporated therein for the passage of primary liquid from first chamber 32 to second chamber 34. Included in outlet port 40 is a hydrophilic membrane 42 which covers outlet port 40 and prevents air from moving between first chamber 32 and second chamber 34 once the membrane has been wet. Second chamber 34 includes an inlet port 44 for the admission of secondary liquid and a number of outlet ports such as port 46 for the passage of primary and secondary liquid, and port 48 for the passage of secondary liquid therefrom. When secondary liquid passes through inlet port 44 into second chamber 34, residual air is trapped in the area below platform 38, outlet port 40 and hydrophilic membrane 42. The presence of this air pocket 45 prevents the passage of primary liquid from first chamber 32 into second chamber 34, because the partial pressure in second chamber 34 is greater than the pressure in first chamber 32 due to the greater pressure of the secondary liquid than the primary liquid.

As further seen in FIG. 2, second chamber 34 includes a reservoir 50 incorporated therein. A flexible diaphragm member 52 is disposed across and seals the upper portion 53 of reservoir 50. When secondary liquid passes into second chamber 34, it is under sufficient pressure to displace diaphragm 52 because the pressure of the secondary liquid is greater than that of the primary liquid. Because diaphragm 52 is displaced, secondary liquid is able to enter reservoir 50 and pass through reservoir 50 and out of port 48.

An additional portion of secondary tube 18 extends from port 48 upon which is positioned secondary flow control 26. Similarly, a portion of primary tube 16 extends from port 46 below combined air barrier and liquid sequencing valve 28. Primary flow control 24 is positioned thereon. Primary tube 16 and secondary tube 18 meet and form common tube 20 which is connected to hypodermic needle 22 for administration of medical liquids to the patient.

In a preferred embodiment, reservoir 50 is integrally formed as part of second chamber 34. Second chamber 34, first chamber 32 and housing 30 all may be constructed of conventional intravenous valve materials such as plastic, metal or glass. Housing 30 may include an air vent 54 positioned proximate the top of housing 30. In one embodiment, covering air vent 54 is a hydrophobic membrane 56 which permits air to vent therethrough but prevents primary liquid from escaping housing 30.

As best seen in FIG. 3 of the drawings, in an alternative embodiment of the invention, combined air barrier and liquid sequencing valve 120 comprises a housing 130 having a first chamber 132, a second chamber 134, a partition 136 between first chamber 132 and second chamber 134, a port 140 between first chamber 132 and second chamber 134, and a hydrophilic membrane 142 covering port 140. An inlet port 144 to second chamber 134 is incorporated in housing 130. At the bottom of second chamber 134 is outlet port 146 which is designed for the passage of primary or secondary liquid.

In operation, primary liquid enters housing 130 through port 135 and passes down port 135 to the bottom of housing 130 and into first chamber 132. The primary liquid then passes upward in first chamber 132 and through port 140 and hydrophilic membrane 142 into second chamber 134. The primary liquid then returns downward in second chamber 134 and out port 146.

A second outlet port 148 is also disposed at the bottom of second chamber 134, but is designed primarily for the passage of the secondary liquid. In this regard, as further seen in FIG. 3, reservoir 150 is disposed in second chamber 134. A flexible diaphragm 152 is disposed across and resiliently seals reservoir 150. When secondary liquid enters second chamber 134 through port 144 the higher pressure of the secondary liquid causes diaphragm 152 to unseat from the top 153 of reservoir 150. This allows passage of secondary liquid into reservoir 150 and out of port 148.

Upon admission of secondary liquid into second chamber 134 through port 144, the air within second chamber 134 rises into an air capturing pocket 155 at the top of housing 130, proximate hydrophilic membrane 142. The presence of this air, which is under greater pressure than the primary liquid due to the force of the secondary liquid upon it, prevents primary liquid from flowing through hydrophilic membrane 142 into second chamber 134. Thus, secondary liquid will flow from second chamber 134 as long as the pressure of the secondary liquid is greater than that of the primary liquid. When the pressure of the secondary liquid becomes less than that of the primary liquid, primary liquid will flow through hydrophilic membrane 142 into second chamber 134 and diaphragm 152 will again seal reservoir 150. Primary liquid will then begin to flow out of port 146.

It should be noted that inlet port 144 includes a tubular passageway 162 from rubber reseal 163 to a point 164 within second chamber 134 below air pocket 155. As a result, when secondary liquid enters second chamber 134, the air within the second chamber 134 is driven into air capturing pocket 155.

As an additional feature, vent 156 is positioned proximate the top 157 of housing 130. Vent 156 allows air within the first chamber 132 to escape. In a preferred embodiment, vent 156 includes hydrophobic membrane 158 which allows the passage of air from first chamber 132 but prevents primary liquid from escaping the chamber.

As further seen in FIGS. 2 and 3 of the drawings, reservoir 50 and 150, respectively, contain diaphragm unseating pins 60 and 60, respectively, which are movably positioned within reservoirs 50 and 150. When diaphragm unseating pins 60 and 160 are moved against diaphragms 52 and 152 they lift the diaphragm off of the top 53 and 153 of reservoirs 50 and 150. Consequently, when primary liquid is present in second chamber 34 and 134, the primary liquid is allowed to enter reservoirs 50 and 150 and thereby pass through ports 48 and 148 respectively and prime the secondary system. Diaphragm unseating pins 60 and 160 may be threadably attached within reservoir 50 and 150, so that screwing pin 160 inward or outwardly exerts the pressure required to unseal diaphragm 152 from reservoir 150, or they may be resiliently movable in rubber sleeves 61 and 161, respectively.

It should be especially noted that while in FIG. 3 housing 130 is divided into first and second chambers by a partition 136 disposed vertically in FIG. 2, partition 36 is disposed horizontally. The present invention encompasses the use of any number of partitions, either vertical or horizontal, which employ the greater pressure of the secondary liquid within an air capturing pocket, to cut off the flow of primary liquid.

As is further seen in FIG. 4 of the drawings, in an alternative embodiment combined air barrier and liquid sequencing valve 228 may comprise housing 230 and having a first chamber 232, a second chamber 234, and a partition 236 which divides housing 230 into the first and second chambers. Raised platform 238 is incorporated into partition 236 and includes port 240, with hydrophilic membrane 242 disposed across and covering port 240. Air capturing pocket 255 comprises the area below port 240 and partition 238. Alternatively, as seen in FIG. 4A, air capturing pocket 255 may also comprise the area below port 240 encircled by a downwardly descending partition 239, which would eliminate the necessity of a raised platform.

In operation, primary liquid flows from primary tube 216 into first chamber 232 through port 235, then passes through port 240 and into second chamber 234. Primary liquid may then pass out of second chamber 234 by means of port 246.

When secondary liquid passes into second chamber 234 through inlet port 244, the air within second chamber 234 is driven into air capturing pocket 255. This air is under greater pressure than the primary liquid within hydrophilic membrane 240. As a result, the flow of primary liquid is halted. Primary flow is regulated by primary flow control 224 which is preferably a screw or roller clamp on primary tube 216. Secondary flow is regulated by secondary flow control 226 which is again preferably a screw or roller clamp on secondary tube 218. Since secondary flow is usually greater than primary flow, secondary flow control 226 will be open to a greater extent than primary flow control 224. Thus, when secondary liquid is depleted there will be a greater draw on the system that can be supplied by primary flow control 224. In order to insure that air is not thereby drawing into the system, an air barrier is incorporated into port 246. This air barrier may be a hydrophilic membrane 247 or a mechanical float valve 249, which closes in the absence of liquid.

The foregoing description and drawings merely explain and illustrate the invention and the invention is not limited thereto except insofar as the appended claims are so limited as those skilled in the art who have the disclosure before them will be able to make modifications and variations therein without departing from the scope of the invention.

We claim:

1. A gravitational flow system for the sequential administration of medical liquids to a patient comprising:
   a primary container suspended in space for containing a primary medical liquid,
   a primary tube having its distal end in fluid communication with said primary container,
   a secondary container suspended in space at a height greater than that of said primary container for containing a secondary medical liquid,
   a secondary tube having its distal end in fluid communication with said secondary container,
   a common tube having its distal end in fluid communication with the proximal ends of said primary and secondary tubes and its proximal end open for the flow of liquid therethrough to form a primary liquid path comprising said primary tube and said common tube and a secondary liquid flow path comprising said secondary tube and said common tube,
   secondary flow control means in said secondary liquid flow path for adjusting the flow rate of said secondary liquid therethrough,
   primary flow control means on said primary tube for adjusting the flow of said primary liquid through said primary liquid flow path at a rate independent of the flow rate of said secondary liquid through said secondary liquid flow path, and
   a combined air barrier and liquid sequencing valve interposed in said primary and secondary flow paths which allows primary liquid to flow from said primary container whenever the height of said primary liquid is less than or equal to the height of said secondary liquid in said system and which prevents primary liquid from flowing from said primary container whenever the height of said primary liquid is less than the height of said secondary liquid in said system,
   said combined air barrier and liquid sequencing valve comprising a housing having an air capturing pocket disposed in the primary liquid flow path through said valve, said air capturing pocket being constructed and arranged for the entrapment of a quantity of air therein during dispensing of secondary liquid whereby the flow of primary liquid is halted.

2. The system defined in claim 1, wherein said housing includes a plurality of partition members disposed substantially horizontally within said housing so as to divide said housing into first and second chambers and to seal said first chamber from said second chamber, said partition member including an outlet port incorporated therein, said outlet port being sealed by a hydrophilic membrane for preventing the movement of air between said first and second chambers, said second chamber further including an inlet port for secondary liquid and a plurality of outlet ports at the bottom thereof for the passage of primary and secondary liquid therefrom.

3. The system defined in claim 2 wherein said air capturing pocket comprises a raised platform portion incorporated in said partition member, and an outlet port incorporated in said raised platform portion whereby air may be entrapped within said raised platform portion during dispensing of secondary liquid.

4. The system defined in claim 2 wherein said air capturing pocket comprises a partition disposed downwardly from said horizontal partition member proximate said outlet incorporated therein whereby air may be entrapped below said outlet port during dispensing of secondary liquid so as to halt the flow of primary liquid.

5. The system defined in claim 1 further including a reservoir incorporated therein, said reservoir including a flexible diaphragm disposed across and selectively sealing same, said flexible diaphragm being constructed and arranged for displacement by said secondary liquid, whereby said secondary liquid may pass into said reservoir and through an outlet port positioned proximate the bottom thereof.

6. The system defined in claim 2, wherein said inlet port to said first chamber is positioned proximate the top thereof and said inlet and outlet ports to said second chamber are respectively positioned proximate the side and bottom thereof.

7. The system defined in claim 5, wherein said reservoir is integrally formed as a portion of said second chamber.

8. The system defined in claim 1 or 2, wherein said first chamber further includes a closable air vent.

9. The system defined in claim 8, wherein said air vent is covered by a hydrdophobic membrane.

10. A gravitational flow system for the sequential administration of medical liquids to a patient, comprising:
    a primary container suspended in space for containing a primary medical liquid,
    a primary tube having its distal end in fluid communication with said primary container for the flow of primary liquid therethrough,
    a secondary container suspended in space at a height greater than that of said primary container for containing a secondary medical liquid,
    a secondary tube having its distal end in fluid communication with said secondary container for the flow of a secondary medical liquid therethrough,
    a common tube having its distal end in fluid communication with the proximal ends of said primary and secondary tubes and its proximal end open for the flow of liquid therethrough to form a primary liquid path comprising said primary tube and said common tube and a secondary liquid flow path comprising said secondary tube and said common tube,
    a secondary flow control means in said secondary liquid flow path for adjusting the flow rate of said secondary liquid therethrough,
    a primary flow control means on said primary tube for adjusting the flow rate of said primary liquid through said primary flow path to a rate independent of the flow rate of said secondary liquid through said secondary liquid flow path, and
    a combined air barrier and liquid sequencing valve having a housing comprising a first chamber which constitutes a portion of said primary tube and has inlet and outlet ports thereto and a second chamber which constitutes a portion of said secondary tube and has inlet and outlet ports thereto, said first chamber having valve means associated therewith which allows liquid to flow from said primary container whenever the height of said primary liquid is greater than or equal to the height of said secondary liquid in said system and which prevents primary liquid from flowing from said primary container whenever the height of said primary liquid is less than the height of said secondary liquid in said system, said second chamber having means associated therewith substantially impervious to air while said set is in use to prevent the flow of air through said secondary flow path.

11. The system defined in claim 10 wherein said means associated with said second chamber is a hydrophilic membrane covering said outlet therefrom.

12. A combined air barrier and liquid sequencing valve for the sequential administration of a primary liquid and a secondary liquid comprising:

a housing divided into two or more chambers by a plurality of partition members, a first chamber in said housing having an inlet port incorporated therein for the passage of primary liquid into said first chamber, and an outlet port incorporated therein for the passage of said primary liquid from said first chamber into the second chamber, said outlet port from said first chamber including a hydrophilic membrane incorporated therein and covered thereby for the prevention of air movement between said first chamber and said second chamber when said hydrophilic membrane is moistened, an inlet port to said second chamber for the admission of secondary liquid and a plurality of outlet ports from said second chamber for the passage of primary or secondary liquid, and an air capturing pocket proximate said hydrophilic membrane covering said outlet port from said first chamber to said second chamber, said air capturing pocket being constructed and arranged for the reception of residual air within said second chamber proximate said hydrophilic membrane when said secondary liquid is dispensed into said second chamber whereby the flow of said primary liquid is interrupted for so long as the pressure of said secondary liquid is greater than that of said primary liquid.

13. The combined air barrier and liquid sequencing valve defined in claim 10 or 12 in which said second chamber further includes a reservoir incorporated therein, said reservoir including a flexible diaphragm member disposed across and selectively sealing one end thereof, and an outlet port in fluid communication with one of said outlet ports from said second chamber for the passage of secondary liquid from said reservoir, said flexible diaphragm member being constructed and arranged for displacement by secondary liquid in said second chamber so as to allow the passage of secondary liquid through said reservoir and out of said second chamber.

14. The combined air barrier and liquid sequencing valve defined in claim 13 further comprising diaphragm unseating means for the manual displacement of said flexible diaphragm member whereby said second chamber and the secondary liquid flowpath may be primed with liquid prior to use in order to prevent passage of air through the secondary liquid flow path.

15. The combined air barrier and liquid sequencing valve defined in claim 14 wherein said diaphragm unseating means comprises a pin member movably mounted so as to displace said diaphragm as required.

16. The combined air barrier and liquid sequencing valve defined in claim 15 wherein said pin member includes a threaded portion rotatably mounted within said housing whereby the force required to displace said flexible diaphragm member may be adjusted as required.

17. The combined air barrier and liquid sequencing valve defined in claim 10 or 12 in which said inlet port to said first chamber is proximate the top of said housing and includes a passageway to the bottom of said housing in fluid communication with said first chamber;

said outlet port from said first chamber to said second chamber is proximate the top of said first and second chamber;

said air capturing pocket being disposed in said second chamber proximate said outlet port; and said inlet port to said second chamber includes a passageway which enters said second chamber at a point below said air capturing pocket, so as to entrap air therein by means of the entrance of said secondary liquid.

18. The combined air barrier and liquid sequencing valve defined in claim 10 or 12 wherein said first chamber further includes a closable air vent.

19. The combined air barrier and liquid sequencing valve defined in claim 18 wherein said air vent is positioned proximate the top of said housing and is covered by a hydrophobic membrane thereby preventing the passage of liquid therefrom.

20. The combined air barrier and liquid sequencing valve defined in claim 2 or 12 wherein said partition member is disposed in a substantially vertical orientation with said first and second chambers being disposed substantially coaxially therefrom.

21. The combined air barrier and liquid sequencing valve defined in claim 20 further including a reservoir incorporated therin for the reception of secondary liquid within said second chamber, said reservoir being constructed and arranged so as to overflow said secondary liquid into said first chamber thereby filling said first chamber and entrapping residual air within said air capturing pocket.

22. The invention according to claim 21 wherein said reservoir is disposed substantially perpendicularly to said diaphragm member.

* * * * *